United States Patent [19]

Sakai et al.

[11] Patent Number: 5,454,971
[45] Date of Patent: Oct. 3, 1995

[54] ALKALINE LIPASE, METHOD FOR PRODUCING THE SAME, MICROORGANISM PRODUCING THE SAME AND DETERGENT COMPOSITION CONTAINING ALKALINE LIPASE

[75] Inventors: Nobuaki Sakai; Masahiro Suzuki; Tatsuya Mizukoshi, all of Tokyo; Yukie Goto, Kanagawa; Keijitsu Tanaka, Tokyo; Michihiro Takama, Tokyo; Norio Moriya, Tokyo; Kazunori Sakimoto, Tokyo, all of Japan

[73] Assignee: Showa Denko K.K., Tokyo, Japan

[21] Appl. No.: 67,075

[22] Filed: May 26, 1993

[30] Foreign Application Priority Data

| May 27, 1992 | [JP] | Japan | 5-160353 |
| Oct. 27, 1992 | [JP] | Japan | 4-311470 |
| Nov. 26, 1992 | [JP] | Japan | 4-317319 |
| Feb. 22, 1993 | [JP] | Japan | 5-032020 |

[51] Int. Cl.$^6$ .................. C11D 17/00; C12N 9/20; C12N 1/00; D06M 16/00
[52] U.S. Cl. .................. 252/174.12; 435/198; 435/264; 435/874
[58] Field of Search .................. 435/198, 264, 435/874; 252/174.12

[56] References Cited

U.S. PATENT DOCUMENTS

| 4,933,287 | 6/1990 | Farin | 435/198 |
| 5,168,060 | 8/1993 | Holmes | 435/198 |

FOREIGN PATENT DOCUMENTS

| 62990 | of 1973 | Japan . |
| 55118 | 12/1985 | Japan . |
| 280274 | 12/1986 | Japan . |
| 222771 | 9/1989 | Japan . |

OTHER PUBLICATIONS

Andree et al, *Journal of Applied Biochemistry*, 2:218–229 (1980).
Sasaki et al, *Biochemical and Biophysical Research Communications*, 70:125–131 (1976).

*Primary Examiner*—Robert A. Wax
*Assistant Examiner*—Hyosuk Kim
*Attorney, Agent, or Firm*—Sughrue, Mion, Zinn, Macpeak & Seas

[57] ABSTRACT

A microorganism belonging to the genus Pseudomonas; an alkaline lipase produced by the microorganism or its mutants; a method of producing the alkaline lipase; and detergents containing the alkaline lipase as an aid, the alkaline lipase having (1) an operative pH of from 4 to 11.5, and an optimum pH of from 7.0 to 9.5, as measured using triolein emulsion as a substrate; (2) an operative temperature of from 10° to 80° C., and an optimum temperature of from 55° to 65° C., as measured using triolein emulsion as a substrate; (3) a molecular weight of 28,000 ± 2,000 as measured by electrophoresis using SDS polyacrylamide; (4) isoelectric point of 4.5 ± 1.5 as measured by isoelectric focusing polyacrylamide gel electrophoresis; and (5) an inhibition of lipase activity by a detergent component of not higher than 50% as measured using sodium linear-alkylbenzenesulfonate as said detergent component.

The alkaline lipase has an improved stability against detergent components such as a surfactant and a protease, and can be blended with a detergent together with a protease. The alkaline lipase is less susceptible to inhibition of lipase activity by a detergent component and can increase washing power of detergents.

10 Claims, 2 Drawing Sheets

ALKALINE LIPASE, METHOD FOR PRODUCING THE SAME, MICROORGANISM PRODUCING THE SAME AND DETERGENT COMPOSITION CONTAINING ALKALINE LIPASE

BACKGROUND OF THE INVENTION

1. Field Of the Invention

The present invention relates to a novel alkaline lipase, method for producing the same, a microorganism producing the lipase and use thereof. More particularly, the present invention relates to a novel lipase having an optimum pH in an alkaline region and being produced by a bacteria belonging to the genus Pseudomonas, method for producing the same, a microorganism producing the same, and a detergent composition containing an enzyme which can hydrolyze lipids in an alkaline pH range, wherein the aqueous solution of said detergent composition has an alkaline pH upon washing.

2. Description Of Related Art

Lipase is used widely as a food processing enzyme for forming flavor of milk products, as a medical enzyme for a digestive, as a diagnostic enzyme for the determination of blood lipid, as an industrial enzyme for the hydrolysis or modification of oils and fats, and so on.

Recently, attention has been paid to the use of lipase as an additive to detergent compositions. It has been known to blend a protease with a detergent composition in order to decompose and remove proteins or the like soil attached to things to be washed. It has also been known to blend a cellulase with a detergent composition in order to remove soil attached to cellulose fiber articles to be washed, or blend a saccharide hydrolyzing enzyme such as an amylase with a detergent composition in order to decompose and remove a saccharide or the like soil attached to an article to be washed. Further, recently, it has been known to blend a lipase with a detergent composition to decompose and remove lipids attached to an article to be washed so that washing efficiency can be increased. This use is described in a report by H. Andree et al., "Lipase as Detergent Components," (Journal of Applied Biochemistry, 2, 218–229 (1980)).

Preferred lipase to be blended with detergent compositions includes alkaline lipases which function at alkaline pH values since the pH of a washing solution is in an alkaline pH range under ordinary washing conditions. In addition, it has been known that while lipid stains can generally be removed relatively readily at high temperatures and under high alkaline conditions, lipid stains cannot be removed sufficiently with washing at low temperatures (60° C. or lower). There has been observed an increasing tendency of washing at a lower temperature not only in Japan where mainly low temperature washing has been performed but also in European countries and U.S.A., and hence preferred lipases to be blended with detergent compositions are those which can act sufficiently at low temperatures. Also, preferred lipases to be blended with detergent compositions are those which can exhibit their function stably upon washing in the presence of detergent components such as a surfactant, and protease that is present in various detergents, or those which is less inhibited by detergent components such as a surfactant, and which are stable when stored as a blend with the detergent composition. There has been a keen desire for the development of a detergent composition which contains a lipase having the aforementioned preferred characteristics and which has a high washing efficacy against lipid soils.

It has been known that microorganisms producing lipases include those belonging to the genera Pseudomonas, Alcaligenes, Achromobacter, Mucor, Candida, Humicola, etc. Most of the lipases produced by these microorganisms have optimum pH values in a range from neutral to a weakly alkaline region, and exhibit poor stability to anionic surfactants. Further, the lipase activity of lipases produced by the microorganisms belonging to the genera Achromobacter, Candida, Mucor, and Humicola is inhibited strongly in copresence of anionic surfactants, respectively.

It has been well known that microorganisms belonging to the genus Pseudomonas produce a lipase. The genus Pseudomonas include various species such as *Pseudomonas fluorescens, Pseudomonas cepacia, Pseudomonas fragi, Pseudomonas alcaligenes, Pseudomonas aeruginosa*. However, known lipases produced by these specified species do not meet the aforementioned characteristics.

Furthermore, productivity of lipase by conventional lipase-producing strains was generally low and hence insufficient for industrial application. In order to solve this problem, it is a usual course to try to improve productivity by means of mutation. Conventional method for improving productivity is to perform a mutational treatment to strains, and select those strains having higher productivity from among all the surviving strains. This conventional method takes a long time and much labor. Therefore, it has been desired strongly to establish a method of producing lipases more efficiently. While for other enzymes, there have been known methods of producing cellulases, proteases or amylases efficiently using strains resistant to Vancomycin or Ristocetin (Japanese Patent Application Laid-Open No. 222771/1989), and a method of producing an α-amylase using a strain resistant to Tunicamycin (T. Sasaki, et al., BIOCHEMICAL AND BIOPHYSICAL RESEARCH COMMUNICATIONS, 70, 125–131, 1976), no report has been made on lipases.

SUMMARY OF THE INVENTION

Accordingly, an object of the present invention is to provide an alkaline lipase which has an optimum DH in an alkaline pH range, is almost free of inhibition of lipase activity by components of a detergent, and has a high stability to components of a detergent such as surfactant or protease.

Another object of the present invention is to provide a method of efficiently producing an alkali lipase having the aforementioned characteristics.

Still another object of the present invention is to provide an enzyme-containing detergent composition comprising, as an enzyme additive, an alkaline lipase having the aforementioned characteristics.

Yet another object of the present invention is to provide an enzyme-containing detergent composition comprising two or more enzymes, including the aforementioned alkaline lipase and a protease.

In order to obtain alkaline lipases having the aforementioned characteristics, the present inventors have isolated and screened many microorganisms for exploration, and as a result, they have found that strains belonging to the genus Pseudomonas, represented by *Pseudomonas mendocina* SD702 isolated from the soil in suburbs of Tokyo, produce novel alkaline lipases which are effective as additive to be blended with detergent compositions.

Also, the present inventors have found that lipases obtained from culture broths of *Pseudomonas mendocina* NCIMB10541, NCIMB10542, or NCIMB10543 have the same characteristics as described above and serve as alkaline lipase effective as an additive to be blended with detergent compositions.

Further, the present inventors have found that productivity of alkaline lipases by lipase-producing microorganisms can be increased greatly by endowing the microorganisms with resistances to antibiotics.

Although there have hitherto been known various lipases produced by various strains, and detergent compositions containing such lipases, there have been known no alkaline lipase derived from *Pseudomonas mendocina* nor detergent composition containing such an alkaline lipase. Thus, the present invention has been completed based on the discovery by the present inventors that a novel alkaline lipase produced by *Pseudomonas mendocina* is very effective as an enzyme to be blended with detergent compositions.

DETAILED DESCRIPTION OF THE INVENTION

Figure 1:
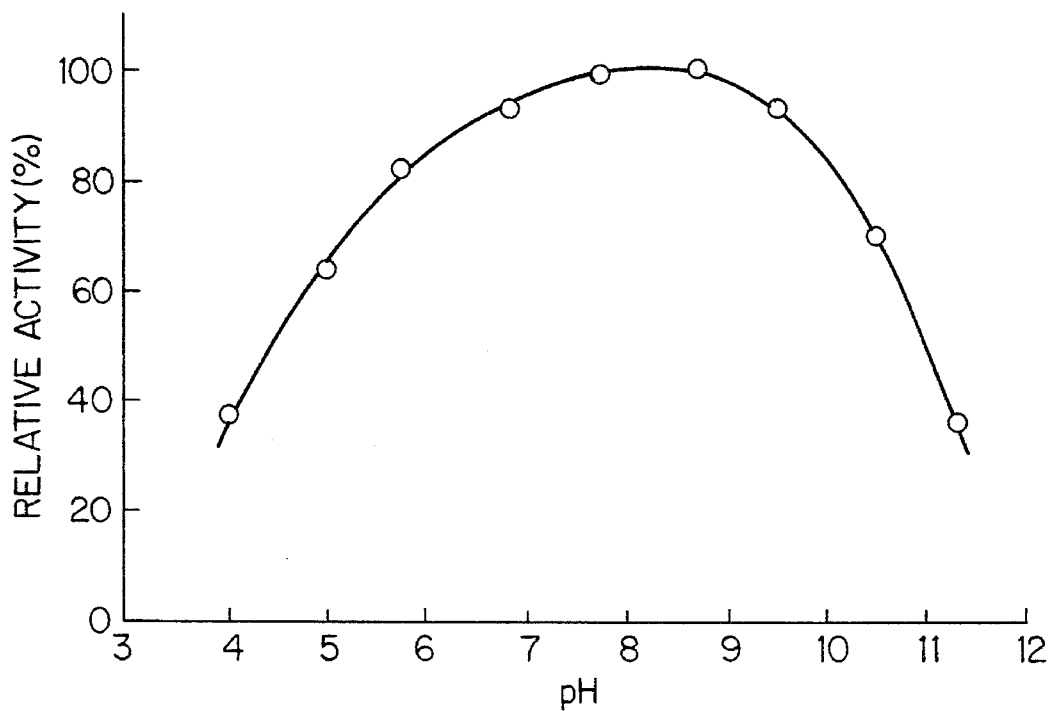
FIG. 1 is a graph illustrating relationship between reaction pH and relative activity of alkaline lipase produced by *Pseudomonas mendocina* SD702.

Hereafter, detailed explanation will be made on the novel strain producing the alkaline lipase of the present invention, the alkaline lipase, method for producing it and its utility.

Alkaline Lipase-Producing Microorganism

The microorganism used for producing the alkaline lipase of the present invention is not limited particularly so far as it is a microorganism which belongs to the genus Pseudomonas that can produce an alkaline lipase. Such a microorganism may be selected from stored strains or those microorganisms newly isolated from the nature. Also, such a microorganism may include spontaneous or artificial mutants thereof so far as they have an ability of producing the alkaline lipase having the characteristics described later on. Microorganism strains can be isolated from soil or other isolation sources by a conventional method. Objective strains can be selected by cultivating microorganisms to be evaluated, for example, in an ordinary culture medium for bacteria, and determining lipase activity of a culture both at a high pH and at room temperature by a conventional method.

In order to prepare mutant strains, for example, a common technique may be used in which an original strain is subjected to an artificial mutation treatment such as exposure to ultraviolet rays or chemicals, e.g., N-methyl-N'-nitro-N-nitrosoguanidine (NTG), and spread over an agar medium containing oil such as olive oil, and colonies whose clear zones formed around them are larger than the clear zone of the original strain are selected, followed by cultivating them in a lipase producing medium, thus screening a strain having the most excellent productivity.

As an example of the strain belonging to the genus Pseudomonas which produces the novel lipase of the present invention, there can be cited a novel strain SD702 isolated by the present inventors from the soil in suburbs of Tokyo. The strain SD702 has the following properties.
(a) Morphology
 (1) Shape and size of cell: Linear rod with a size of 0.5 to 0.7×2.2 to 3.3 µm.
 (2) Polymorphism of cell: None.
 (3) Motility: Yes, polar monotrichous flagella.
 (4) Spore formation: No.
 (5) Gram stain: Negative.
 (6) Acid-fast stain: Negative.
(b) Growth on the following media:
 (1) Meat broth agar plate medium:
  Spreading and smooth colonies without pigment production.
 (2) Meat broth agar slant medium:
  Spreading growth and smooth edge. No pigment.
 (3) Meat broth liquid medium:
  Grows all over the medium, with forming precipitates.
 (4) Meat broth gelatin stab culture medium:
  Grows only on the upper portion of the medium.
  No liquefaction.
 (5) Litmus milk:
  Weakly alkaline. No coagulation.
(c) Physiological Properties
 (1) Reduction of nitrates: Positive.
 (2) Denitrification reaction: Negative.
 (3) MR test: Negative.
 (4) VP test: Negative.
 (5) Production of Indole: Negative
 (6) Production of hydrogen sulfide: Negative.
 (7) Hydrolysis of starch: Negative.
 (8) Assimilation of citric acid: Positive.
 (9) Assimilation of inorganic nitrogen:
  Assimilates nitrates and ammonium salts.
 (10) Production of pigments: Produces water-insoluble pigments. No production of water-soluble pigments and fluorescent pigments.
 (11) Urease: Negative.
 (12) Oxidase: Positive.
 (13) Catalase: Positive.
 (14) Growth pH range: Grows at pH 5 to 12.5.
 (15) Growth temperature range: Grows at 5° to 43° C.
 (16) Behavior to oxygen: Aerobic.
 (17) O-F test: Oxidation.
 (18) Production of acid and gas from sugars:
  Produces acids from D-glucose, D-fructose and glycerol but no gas production.
  Produces no acid nor gas from L-arabinose, D-xylose, D-mannose, D-galactose, maltose, sucrose, lactose, trehalose, D-sorbitol, inositol and starch.
(d) Other properties:
 (1) Resistance to sodium chloride: Grows in the presence of NaCl up to 7%.
 (2) Decomposition of fats: Decomposes Tween 80, tributyrin, triacetin, vegetable oils, etc.
 (3) Assimilation of carbon compounds:
  Assimilates glucose and geraniol.
  Does not decompose starch.
  Does not liquefy gelatin.

(4) Vitamin requirement: Negative.
(5) Accumulation of PHB: Negative.
(6) Arginine dihydratase: Positive.
(7) Phenylalanine deamination reaction: Negative.

The aforementioned bacteriological characteristics of the strain SD702 of the present invention were compared with other strains, consulting "Bergey's Manual of Systematic Bacteriology (1984)", and as a result it is identified to be a bacterium belonging to *Pseudomonas mendocina*. This strain has been deposited at Fermentation Research Institute (renamed as National Institute of Bioscience and Human-Technology since January 1, 1993), Agency of Industrial Science and Technology, Ministry of International Trade and Industry, Japan under Accession No. FERM P-12944 on May 1, 1992 and transferred to the deposit under "Budapest Treaty on the International Recognition of the Deposit of Microorganisms for the Purpose of Patent Procedure" under Accession No.. FERM BP-4291 on May 12, 1993.

Cultivation Method

Upon production of the lipase of the present invention, the alkaline lipase-producing bacterium belonging to the genus Pseudomonas is cultivated using an appropriate medium. As the nutrient sources of the medium, any medium usually used for the cultivation of microorganisms may be used so far as the microorganisms of the present invention can grow thereon and produce alkaline lipase. Carbon source may be any assimilable carbon compounds or those containing them, for example, glucose, glycerol, oils and fats, corn steep liquor, Tween surfactants, etc. Nitrogen source may be any assimilable nitrogen compounds or those containing them, for example, ammonium salts, nitrates, soybean powder, beef extract, corn steep liquor, farmamedia, etc. In addition, as the inorganic salts there can be used salts such as phosphoric acid salts, and magnesium salts.

Cultivation may be carried out under conditions most advantageous to the production of alkaline lipases, objective of production, although such conditions may vary more or less depending on the composition of the culture medium used. The cultivation temperature may be within the range of 10° to 40° C., preferably 20° to 37° C. The cultivation time may be within the range of about 8 to 100 hours, and the cultivation may be stopped when the alkaline lipase production reaches a maximum value. The pH of the medium may preferably be 7 to 9.5, which is preferable for the production of alkaline lipases. As a result of, cultivation under the aforementioned conditions, the objective alkaline lipase can be obtained as secreted enzyme in the culture broth.

Isolation and Purification Methods

The alkaline lipase of the present invention thus produced can be isolated from the culture broth and purified in a conventional method generally used for collecting lipases.

That is, cells and solid substances can be removed by centrifugation, filtration or the like to obtain a supernatant or filtrate. From the solution thus separated, with or without concentration, the alkaline lipase of the present invention can be obtained by a salting out method in which proteins are precipitated by adding soluble salts, an organic solvent precipitation method in which enzymes or contaminants are precipitated by adding hydrophilic organic solvents, an absorption-elution method using ion exchange resins, a gel filtration method, a spray drying method with or without adding stabilizing aids, a lyophilization method or the like, singly or in combination.

Antibiotic-Resistant Bacterium Strain and Production of Alkaline Lipase Using the Same As a result of extensive investigation on improvement in the lipase productivity of lipase-producing bacteria, the present inventors have found that the lipase productivity can be increased by endowing the lipase-producing strain with resistance to antibiotics. For example, it has been confirmed that artificial or spontaneous mutant strains belonging to the genus Pseudomonas and having resistance to Streptomycin produce lipase in the medium in remarkable amounts. The term "resistance to Streptomycin" as used herein means an ability of growing in the presence of Streptomycin in a concentration too high for ordinary bacteria to grow, for example, in the presence of Streptomycin in a concentration on the order of generally several tens ppm which may vary depending on the kind of strain.

Also, it has been found that lipase productivity can be increased greatly by endowing, for example, a lipase-producing bacterium with resistance to a cell wall synthesis inhibitor which is a kind of antibiotics. The term "resistance to a cell wall synthesis inhibitor" as used herein refers to an ability of growing in the presence of a cell wall synthesis inhibitor in a concentration too high for ordinary bacteria to grow, for example, in the presence of the inhibitor in a concentration on the order of generally several tens ppm which may vary depending on the kind of strain.

That is, the present invention also provides a method of producing a lipase using a lipase-producing bacterium having a resistance to an antibiotics. Furthermore, the present invention provides a bacterium having a resistance to an antibiotics and which is useful for the production of an enzyme such as lipase.

In the present invention, the antibiotics-resistant bacterium can be obtained, for example, by cultivating a lipase-producing bacterial strain with which the resistance to a desired antibiotics is to be endowed (parent or original strain) in a suitable medium, irradiating cells of the strain with ultraviolet rays or x rays, or treating them with a known chemical mutagen such as ethyl methanesulfonate (EMS), N-methyl-N'-nitro-N-nitrosoguanidine (NTG) or p-dimethylaminobenzene-diazosulfonic acid, washing it properly, adjusting their population properly, spreading them over an agar medium containing an antibiotics in a concentration in which the parent strain cannot grow (minimum growth inhibitory concentration (MIC)), for example, several tens ppm of Streptomycin or about 100 ppm of a cell wall synthesis inhibitor, and collecting antibiotics-resistant colonies which are resistant to Streptomycin or the cell wall synthesis inhibitor. Surprisingly, many of the antibiotics-resistant strains thus obtained produce lipases in amounts larger than the parent strain. Among these strains, high lipase-producing strains can be screened.

Mutant strains having further increased lipase productivities may be obtained from the antibiotics-resistant strains thus obtained by artificial or spontaneous mutation. The present invention also encompasses such mutant strains and methods of producing lipases by cultivating such mutant strains.

More specifically, representative examples of the antibiotics-resistant lipase-producing bacteria which can be used in the present invention include Streptomycin-resistant strains such as Pseudomonas SD703 (FERM P-13307/ FERM BP- 4292) derived from *Pseudomonas mendocina* NCIMB10541 as a parent strain by the aforementioned procedure, and cell wall synthesis inhibitor-resistant strains such as *Pseudomonas mendocina* SD704 (FERM P-13357/

FERM BP-4293) derived from *Pseudomonas mendocina* NCIMB10541 as a parent strain by the aforementioned procedure. The three strains, *Pseudomonas mendocina* NCIMB10541, *Pseudomonas mendocina* NCIMB10542, *Pseudomonas mendocina* NCIMB10543, are easily obtained from the National Collection of Industrial and Marine Bacteria, Aberdeen, Scotland, United Kingdom. Their bacteriological characteristics are described in Bergey's Manual of Systematic Bacteriology (1984)). The bacteriological characteristics of the Streptomycin-resistant strains such as Pseudomonas SD703 are substantially the same as those of the parent strain except for degrees of resistance to Streptomycin and lipase productivity. Likewise, the bacteriological characteristics of the cell wall synthesis inhibitor-resistant strains such as *Pseudomonas mendocina* SD704 are substantially the same as those of the parent strain except for degrees of resistance to cell wall synthesis inhibitors and lipase productivity.

The term "antibiotics" as used herein refers to substances which inhibit the growth of microorganisms or cells of other organisms. The antibiotics used in the present invention are not limited particularly, and any antibiotics may be used that are classified usually under a cell wall synthesis inhibitor, a protein synthesis inhibitor, a nucleic acid synthesis inhibitor, or an antibiotics which gives damages to cell membrane structure. The cell wall synthesis inhibitor includes, for example, β-lactam antibiotics, antibiotics affecting a lipid cycle, and antibiotics inhibiting take-up of D-alanine. Examples of the β-lactam antibiotics include Carbenicillin, Penicillin, and Ampicillin. Examples of the antibiotics affecting a lipid cycle include Vancomycin, Ristocetin, Enramycin, Macarbomycin, and Moenomycin. The antibiotics inhibiting D-alanine take-up includes D-cycloserine, etc. The other cell wall synthesis inhibitors include, for example, Tunicamycin. The protein synthesis inhibitor includes, for example, Streptomycin, and Spectinomycin. The nucleic acid synthesis inhibitor includes, for example, Rifamycin.

The lipases of the present invention with the antibiotics-resistant bacteria can be produced by using culture media, cultivation conditions and method of collection of bacterial cells from culture broths which are similar to those used in the aforementioned production method using bacteria which are not resistant to antibiotics.

Any culture medium may be used in the present invention so far as it allows growth of bacterial strains. For example, any carbon source can be used so far as it is or contains at least one assimilable carbon compound, for example, glucose, starch or starch hydrolysate such as liquid starch, molasses, glycerol, oils and fats, corn steep liquor, and Tween surfactants. Any nitrogen source may be used so far as it is or contains at least one assimilable nitrogen compound, for example, an organic nitrogen source such as soybean powder, beef extract, farmamedia, or corn steep liquor, and an inorganic nitrogen source such as an ammonium salt or a nitrate.

In addition, there may suitably be added one or more mineral salts usually used in the cultivation of bacteria, such as phosphates, e.g., secondary phosphate, magnesium salts, calcium salts, manganese salts.

Cultivation can be performed under aerobic conditions, for example, by an aerated stirring method or a shaking culture method.

Cultivation may be performed at a temperature within the range of 10° to 40° C., preferably 20° to 37° C. It is sufficient to maintain pH within the range of 5 to 12 over the whole period of cultivation, with initial pH being preferably within the range of 7 to 9.5. While cultivation time is usually within the range of 8 to 100 hours, it is sufficient to stop the cultivation when the amount of lipase accumulated has reached a plateau. From economical viewpoint, it is preferred to continue cultivation within the range of 20 to 50 hours. Although the productivity of lipase by antibiotic-resistant strains varies greatly depending on the composition of the culture medium and cultivation conditions used, the mutant strains can produce lipases in amounts at least by 1.5 to 2 times as much as the amount of lipase produced by each parent strain in whatever cultivation conditions within the ranges described above.

After the cultivation as described above, collection of lipase from the culture broth can be performed by the known method as described above.

Assay of Enzyme Activities

The activity of the alkaline lipase of the present invention thus obtained was assayed by TLC-FID method using triolein-polyvinyl alcohol (PVA) emulsion as a substrate, or pH star titration method using olive oil-PVA or olive oil-gum arabic as a substrate.

The TLC-FID method was carried out as follows.

A mixture of 0.1 ml of an enzyme solution, 0.4 ml of 100 ml4 Tris buffer solution (pH 9.0), and 0.5 ml of triolein emulsion was reacted in a test tube with a plug while heating at 37° C. for 10 minutes. Then, the reaction was stopped with 0.2 ml of 1N hydrochloric acid. The triolein emulsion used was prepared by adding 1.5 g of triolein to 15 ml of a 2% aqueous PVA solution (POVAL PVA117 (trade name for a product by Kuraray Co., Ltd.) : POVAL PVA205 (trade name for a product by Kuraray Co., Ltd.)= 9: 1), and homogenizing the mixture at 18,000 rpm for 10 minutes while ice-cooling. After the reaction was stopped, 2 ml of n-hexane, 2 ml of isopropyl alcohol and 1 ml of deionized water was added to the reaction mixture, and the resultant mixture was vigorously stirred. After the mixture was allowed to stand, n-hexane layer was extracted, and the oleic acid content thereof was determined by the TLC-FID method (Minagawa et al., Lipids, 18, 7.32, 1983). As for the unit of activity, the amount of enzyme which forms 1 μmol/minute of oleic acid is defined as unity (U).

Specifically, the pH stat titration method was carried out as follows.

The olive oil-gum arabic emulsion used as a substrate was prepared by adding 10 g of gum arabic and 100 g of water to 10 g of olive oil, and homogenizing the resulting mixture at 25,000 rpm for 10 minutes while ice-cooling. On the other hand, the olive oil-PVA emulsion was prepared by adding 100 ml of the aforementioned 2% aqueous PVA solution to 10 g Of olive oil, and homogenizing the resulting mixture at 18,000 rpm for 10 minutes while ice-cooling.

Then, a mixture of 5 ml of the substrate emulsion thus prepared, 5 ml of 10 mM Tris buffer solution (pH 9.0) containing 110 mM NaCl, 4.5 ml of water, and 0.5 ml of an enzyme solution was reacted at 30° C. and at pH 9. The fatty acid generation rate of the reaction mixture was determined from titration rate of 0.05N NaOH. The amount of the enzyme which forms 1 μmol per minute of a fatty acid was defined as unity (U).

In addition, the activity of protease was determined by the method described in Japanese Patent Publication No. 55118/1985, the activity being expressed in terms of nkatal (nanokatal= $10^{-9}$ katal).

Properties of Enzyme

The properties of alkaline lipase produced by *Pseudomonas mendocina* SD702 referred to above, as an example of the alkaline lipase of the present invention, are described below.

(1) Action

Acts on glycerides, and hydrolyzes ester bonds therein.

(2) Substrate Specificity

Hydrolyzes a wide variety of glycerides, esters, etc.

As the glyceride substrate, there were used glyceride-gum arabic emulsions. The emulsion-used was prepared by adding 10 g of gum arabic and 100 g of water to 10 g of each glyceride, and homogenizing the resulting mixture at 25,000 rpm for 10 minutes while ice-cooling.

Then, a mixture of 5 ml of the substrate emulsion thus prepared, 5 ml of 10 mM Tris buffer solution (pH 9.0) containing 110 mMNaCl and 26 mM $CaCl_2.2H_2O$, 4.5 ml of water, and 0.5 ml of an enzyme solution was reacted at 30° C. and at pH 9. The fatty acid generation rate of the reaction mixture was determined from titration rate of 0.05N NaOH by the pH stat titration method. The fatty acid generation rate was defined as decomposition titer of each substrate.

Assuming the decomposition titer for triolein is 100, relative activity of tributyrin is 101, for olive oil 100, for soybean oil 113, and for cotton seed oil 101.

The decomposition titers for esters were determined by colorimetry ($OD_{405}$) of p-nitrophenol produced by hydrolysis reaction at pH 9.0 and at 30° C. of p-nitrophenyl fatty acid ester as a substrate.

Assuming the decomposition titer for pNPP (p-nitrophenyl palmirate) is 100, relative activity of pNPV (p-nitrophenyl valerate) 34, and for pNPB (p-nitrophenyl butyrate) 17.

(3) Operative pH and optimum pH

Behavior of the enzyme toward pH was examined by determining its titers measured by the TLC-FID method using triolein emulsion as a substrate at different pH values within the rage of pH 4.0 to 11.5, using a mixed buffer solution consisting of 100 mM ε-aminocaproic acid, 100 mM bis-Tris(bis(2-hydroxyethyl)iminotris(hydroxymethyl)methane) and 100 mM TAPS (N-tris(hydroxymethyl)methyl-3-aminopropanesulfonic acid) whose pH was adjusted with hydrochloric acid or NaOH. Relationship between reaction pH and relative activity is as shown in FIG. 1. Operative pH is within the range of 4 to 11.5, and optimum pH is within the range of 7.0 to 9.5.

(4) Operative temperature and optimum temperature.

Figure 2:
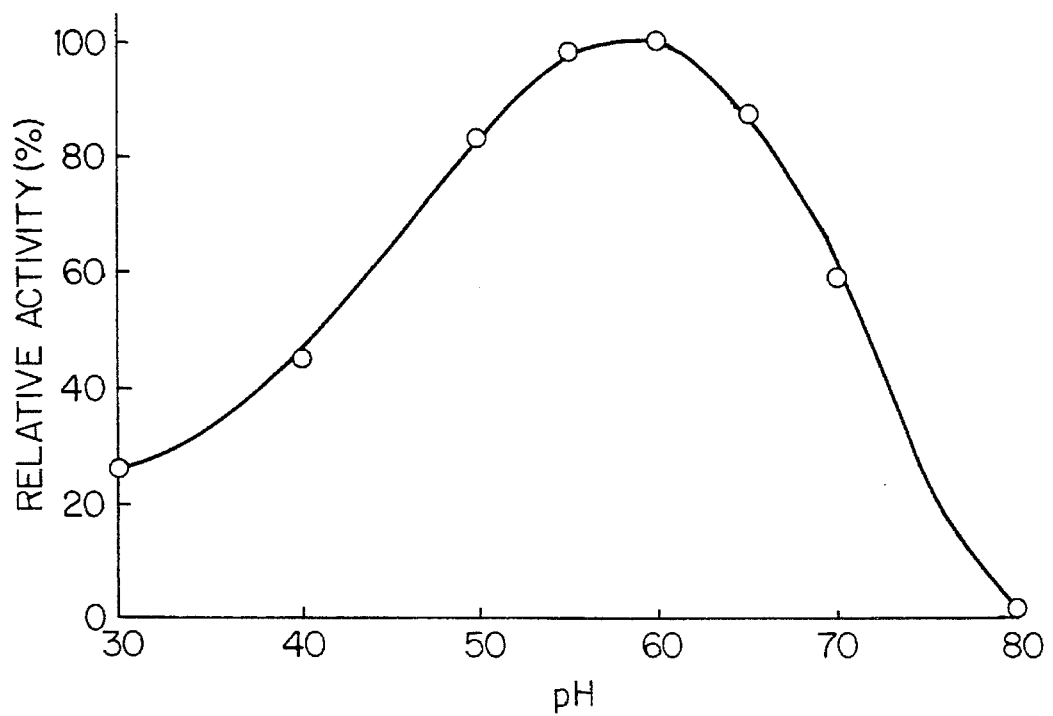
FIG. 2 is a graph illustrating relationship between reaction temperature and relative activity of alkaline lipase produced by *Pseudomonas mendocina* SD702.

Reaction temperature of the enzyme was examined in the same manner as the titration by the TLC-FID method described above except that the reaction was carried out at a fixed pH of 9 and at different temperatures within the range of 30° to 80° C. Relationship between reaction temperature and relative activity is as shown in FIG. 2. Operative temperature is within the range of 30° to 80° C., and optimum temperature is within the range of 55° to 65° C. At temperatures of 40° and 70° C., the enzyme exhibits about 50% of the activity at the optimum temperature.

(5) Temperature stability

Figure 3:
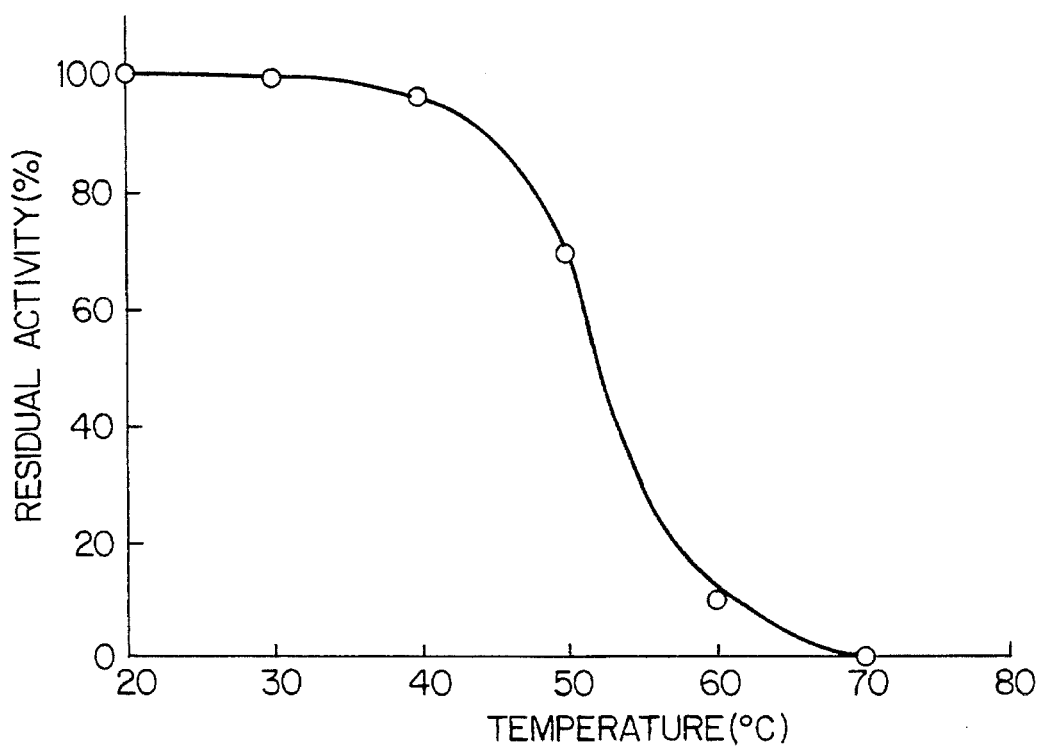
FIG. 3 is a graph illustrating residual activity of alkaline lipase produced by *Pseudomonas mendocina* SD702 after being treated at pH 8 and at various temperatures for 1 hour.

FIG. 3 shows the residual activity of the enzyme after being kept at a different temperature within the range of 20° to 70° C. at pH 8 for 1 hour, determined by the TLC-FID method. Treatments at 30° C. or 40° C. for 1 hour caused substantially no deactivation while treatment at 70° C. for 1 hour mostly resulted in deactivation.

(6) pH Stability

Figure 4:
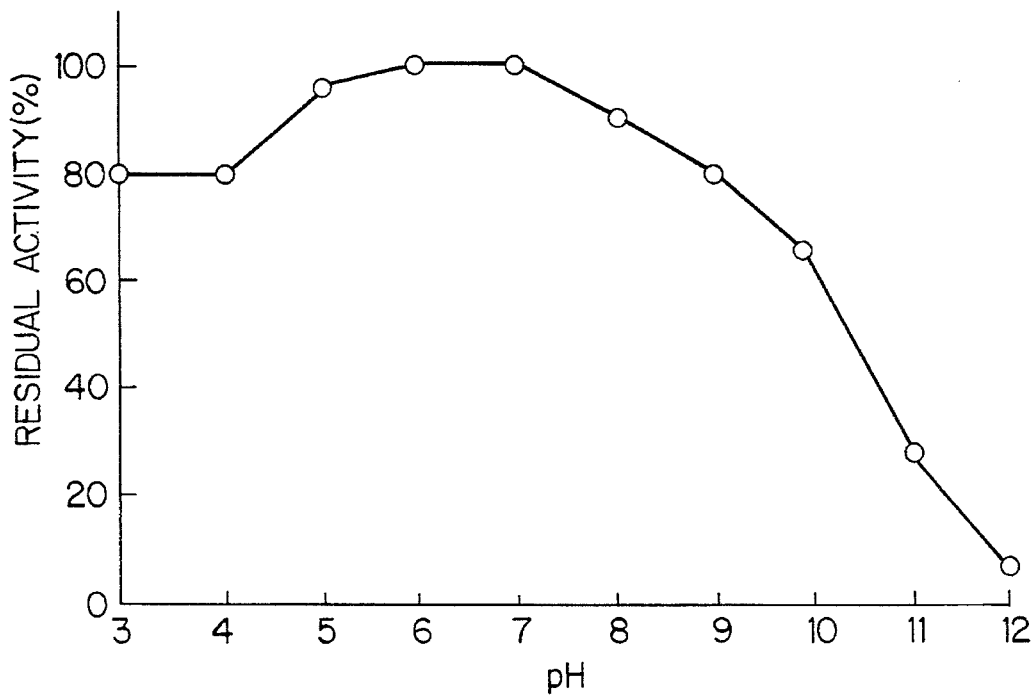
FIG. 4 is a graph illustrating residual activity of alkaline lipase produced by *Pseudomonas mendocina* SD702 after being retained at various pH values and at 37° C. for 1 hour.

FIG. 4 shows the residual activity of the enzyme after being kept at a different pH within the range of pH 3 to 12 at 37° C. for 1 hour, determined by the TLC-FID method. The enzyme retains at least 80% residual activity after treatment at pH 3 to 9. The buffer solutions used were as follows:

pH 3: Glycine-hydrochloric acid;
pH 4 to 5: Acetic acid-sodium acetate;
pH 6 to 7: Phosphoric acid
pH 8 to 9: Tris-hydrochloric acid;
pH 10 to 12: Glycine-NaOH.

(7) Molecular weight

Molecular weight of the enzyme determined by SDS-polyacrylamide gel electrophoresis (molecular weight standard: cytochrome C (monomer, dimer, trimer, tetramer, hexamer)) was 28,000±2,000.

(8) Isoelectric point

The isoelectric point of the enzyme determined by isoelectric focusing polyacrylamide gel electrophoresis was 4.5±1.5.

(9) Influence of detergent components on the enzyme

Solutions of commercially available detergents (4 kinds) in standard use concentrations (1.2 to 5 g/liter), and solutions prepared by adding API-21 (Japanese Patent Publication No. 55118/1985), a typical alkaline protease for detergents, in a concentration of 0.3 nkat/ml to solutions of commercially available detergents (4 kinds) in standard use concentrations were each mixed with 5 mM or 2.5 mM of $CaCl_2.2H_2O$. Then, the alkaline lipase of the present invention was added to each of the resultant mixtures and each mixture was allowed to stand at pH 10 and at 30° C. Residual activity of the alkaline lipase in each mixture was determined by the TLC-FID method immediately after the addition of the enzyme or after 30 minutes therefrom. Results obtained shown in Table 1 indicate that the enzyme of the present invention is highly stable in detergent solutions.

TABLE 1

| | | Concentration | Relative Activity (%) | | | | |
| --- | --- | --- | --- | --- | --- | --- | --- |
| | Concentration of Detergent | of Calcium Added | Enzyme | Enzyme + Detergent After | | Enzyme + Detergent + Protease After | |
| Detergent | (g/liter) | (mM) | only | 0 Minute | 30 Minutes | 0 Minute | 30 Minutes |
| A | 5.0 | 5.0 | 100 | 160 | 136 | 160 | 106 |
| B | 5.0 | 5.0 | 100 | 140 | 106 | 136 | 98 |
| C | 5.0 | 5.0 | 100 | 136 | 102 | 136 | 94 |
| D | 1.2 | 2.5 | 100 | 128 | 159 | 154 | 177 |

The activity of the alkaline lipase produced by strain SD702 was determined in a solution containing 300 ppm of sodium linear-alkylbenzenesulfonate (LAS) and 5 mM $CaCl_2.2H_2O$ solution at pH 10 and at 30° C. by the pH stat titration method using olive oil-PVA emulsion as a substrate. In this case, inhibition of the activity was not higher than 50%, which indicates that inhibition of the activity of the enzyme of the present invention by LAS is very low.

Further, solutions of commercially available detergents (5 kinds) in standard use concentrations (1.2 to 5 g/liter), each containing alkaline protease API-21 (Japanese Patent Publication No. 55118/1985) in a concentration of 0.3 nkat/ml were each mixed with 5 mM or 2.5 mM of $CaCl_2 \cdot 2H_2O$. Then, the alkaline lipase produced by strain SD702 was added to each of the resultant mixtures and the reaction by using olive oil-gum arabic emulsion as a substrate was allowed to proceed at pH 10 and at 30° C. Residual activity of the alkaline lipase in each reaction mixture was determined by the pH stat titration method. Results obtained shown in Table 2 indicate that the enzyme of the present invention is less susceptible to inhibition of lipase activity in solutions of commercially available detergents.

TABLE 2

| Detergent | Concentration of Detergent (g/liter) | Concentration of Calcium Added (mM) | Relative Activity (%) | |
|---|---|---|---|---|
| | | | Enzyme Only | Enzyme + Detergent + Protease |
| A | 5.0 | 5.0 | 100 | 83 |
| B | 5.0 | 5.0 | 100 | 42 |
| C | 5.0 | 5.0 | 100 | 41 |
| D | 1.2 | 2.5 | 100 | 43 |
| E | 2.0 | 2.5 | 100 | 78 |

ADVANTAGE OF THE INVENTION

Since it has a high optimum pH within the range of 7.0 to 9.5 and high stability against detergent components such as surfactants and protease, as well as less inhibition of activity by the detergent components, the alkaline lipase of the present invention can decompose and remove oily soils under washing conditions, and therefore addition thereof to detergents results in increase of the washing power of the detergents. Further, the antibiotic-resistant strains of the present invention have lipase productivities of at least 1.5 to 2.5 times as high as that of the parent strain from which they are derived, and therefore they can be used advantageously in industrial production of lipases.

PREFERRED EMBODIMENTS FOR CARRYING OUT THE INVENTION

Hereinafter, the present invention will be described in detail by examples, reference examples, and comparative examples. However, the present invention should not be construed as being limited thereto. Unless otherwise indicated specifically, all percentages (%) in the following description are by weight.

Example 1: Cultivation of Alkaline Lipase-Producing Bacterium (strain SD702)

A test tube of 18 mm in diameter was charged with 2 ml of a liquid medium containing 2% soybean powder, 2% glucose, 0.1% diammonium hydrogen phosphate., 0.5% dipotassium hydrogen phosphate, 0.1% magnesium sulfate heptahydrate, and 0.3% sodium carbonate, and sterilized in an autoclave at 121° C. for 20 minutes. Then, a loopful of *Pseudomonas mendocina* SD702 was inoculated in the medium and cultivated at 35° C. for 24 hours and at 130 rpm. After the cultivation, bacterial cells were removed by centrifugation to obtain a solution of alkaline lipase. The enzyme solution had a lipase activity of 5 U/ml.

Example 2: Cultivation of Alkaline Lipase-Producing Bacterium (strain SD702) and. Collection of Alkaline Lipase A 5-liter jar fermenter was charged with 2 liters of a liquid medium containing 2% soybean powder, 2% glucose, 0.1 % diammonium hydrogen phosphate, 0.5% dipotassium hydrogen phosphate, 0.1% magnesium sulfate heptahydrate, 0.3% sodium carbonate, and 1.0% of Tween 85, and sterilized in an autoclave at 121° C. for 20 minutes. Then, *Pseudomonas mendocina* SD702 was inoculated in the medium, and cultivated at 35° C. for 20 hours and at 1,000 rpm with stirring and aeration. After the cultivation, bacterial cells were removed by centrifugation to obtain a solution of alkaline lipase. The enzyme solution had a lipase activity of 20 U/ml.

From the alkaline lipase solution the lipase fractions were precipitated at 30 to 50% acetone concentration by a conventional acetone precipitation method. The precipitates were dissolved in deionized water, and precipitates were obtained from the resulting solution at 20 to 40% ammonium sulfate by a conventional ammonium sulfate precipitation method. The precipitates were dissolved in 10 mM Tris-hydrochloric acid buffer solution (pH 7), and the solution was desalted and lyophilized to obtain crude alkaline lipase powder.

Example 3: Purification of Alkaline Lipase

The crude alkaline lipase powder obtained in Example 2 was dissolved in 10 mM Tris-hydrochloric acid buffer solution (pH 7), and dialyzed against 10 mM Tris-hydrochloric acid buffer solution (pH 7) containing 10% ammonium sulfate, followed by hydrophobic chromatography with Butyl-Toyopearl (trade name for a product by Tosoh Co., Ltd.). The active fractions were further fractionated by the same hydrophobic chromatography to obtain active fractions. The active fractions were dialyzed against 10 mM Tris-hydrochloric acid buffer solution (pH 6) containing 1 mM calcium chloride, and then purified by ion exchange chromatography using DEAE-Celluofine A-800 (trade name for a product by Seikagaku Kogyo Co., Ltd.) as adsorbent and NaCl solution as eluent to obtain active fractions, and the fractions was desalted and lyophilized to obtain purified enzyme.

The lyophilized preparation was confirmed to be homogeneous by polyacrylamide gel electrophoresis.

Examples 4 to 6: Cultivation of Strains NCIMB10541, NCIMB10542, and NCIMB10543 and Collection of Alkaline Lipase A 5-liter jar fermenters were each-charged with 2 liters of a liquid medium containing 2% soybean powder, 2% glucose, 0.1% diammonium hydrogen phosphate, 0.5% dipotassium hydrogen phosphate, 0.1% magnesium sulfate heptahydrate, 0.3% sodium carbonate, and 1.0% of Tween 85, and sterilized in an autoclave at 121° C. for 20 minutes. Then, seed culture of *Pseudomonas mendocina* NCIMB10541, NCIMB10542, or NCIMB10543 was inoculated in the medium, and cultivated at 35° C. for 20 hours and at 1,000 rpm with stirring and aeration. After the cultivation, bacterial cells were removed by centrifugation to obtain a solution of alkaline lipase. In this manner alkaline lipase solutions were obtained from the strains NCIMB10541, NCIMB10542, and NCIMB10543, respectively. The enzyme solutions had lipase activities of 16 U/ml, 12 U/ml, and 16 U/ml, respectively.

From the alkaline lipase solutions the lipase fractions were precipitated at 30 to 50% acetone concentration by a conventional acetone precipitation method. The precipitates were dissolved in deionized water, and precipitates were obtained from the resulting solutions at 20 to 40% ammonium sulfate by a conventional ammonium sulfate precipitation method. The precipitates were each dissolved in 10 mM Tris-hydrochloric acid buffer solution (pH 7), and the resulting solutions were each desalted and lyophilized to obtain crude alkaline lipase powders.

Reference Example 1: Minimum Growth Inhibitory Concentration (MIC) of Streptomycin on strain NCIMB10541

Strain NCIMB10541 was spread over culture media of Formulation 1 below which further contained Streptomycin in different amounts to obtain MIC of Streptomycin on the strain. That is, a loopful of a suspension of strain NCIMB10541 (population: $10^8$ cells/ml) was spread over the Streptomycin-added media of Formulation 1, which were incubated at 35° C. for 1 day, and the surface growth of the strain was visually observed. Results obtained are shown in Table 3.

| Formulation 1: | |
|---|---|
| Peptone | 1.0% |
| Yeast extracts | 0.5% |
| Sodium chloride | 0.5% |
| Sodium carbonate | 0.3% |
| Agar | 2.0% |

The media were sterilized in an autoclave at 121° C. for 20 minutes.

TABLE 3

| Concentration of Streptomycin | Surface Growth |
|---|---|
| No addition (control) | +++ |
| 6 ppm | ++ |
| 12 ppm | + |
| 25 ppm | ± |
| 50 ppm | − |
| 100 ppm | − |

Notes:
+++; grows very well
++; grows well
±; grows slightly
+; grows
−; no growth From the results shown in Table 3, it can be seen that MIC of Streptomycin on strain NCIMB10541 was about 50 ppm.

Reference Example 2: Minimum Growth Inhibitory Concentration (MIC) of Carbenicillin on strain NCIMB10541

Strain NCIMB10541 was spread over the culture media of Formulation 2 below which further contained Carbenicillin in different amounts to obtain MIC of Carbenicillin on the strain. That is, a loopful of a suspension of strain NCIMB10541 (population: $10^8$ cells/ml) was spread over the Carbenicillin-added media of Formulation 2, which were incubated at 35° C. for 1 day, and the surface growth of the strain was visually observed. Results obtained are shown in Table 4.

| Formulation 2: | |
|---|---|
| Peptone | 1.0% |
| Yeast extracts | 0.5% |
| Sodium chloride | 0.5% |
| Agar | 2.0% |

The media were sterilized in an autoclave at 121° C. for 20 minutes.

TABLE 4

| Concentration of Carbenicillin | Surface Growth |
|---|---|
| No addition (control) | +++ |
| 13 ppm | +++ |
| 25 ppm | ++ |
| 50 ppm | + |
| 100 ppm | − |
| 200 ppm | − |
| 400 ppm | − |

Notes:
+++; grows very well
++; grows well
+; grows
−; no growth

From the results shown in Table 4, it can be seen that MIC of Carbenicillin on strain NCIMB10541 was about 100 ppm.

Example 7

Strain NCIMB10541 was cultivated on a plate medium of Formulation 1 above at 35° C. for 16 hours, and a loopful amount thereof was inoculated in 5 ml of a liquid medium having a composition of Formulation 1 above excepting agar, charged in a test tube with a Morton plug. The strain was cultivated for 5 hours, and the culture broth was centrifuged. The bacterial cells thus collected were suspended in physiological saline. An N-methyl-N'-nitro-N-nitrosoguanidine (NTG) solution was added thereto to a final concentration of 100 ppm, and the mixture was left to stand at 30° C. for 10 minutes. Then, bacterial cells were collected by centrifugation, washed with physiological saline, and cultivated with shaking at 35° C. for 16 hours in the liquid medium having a composition of Formulation 1 excepting agar. The culture broth was spread over a plate medium of Formulation 1 containing 200 ppm of Streptomycin after it was diluted properly so that a viable cell population became about $10^8$ cells per plate. Most of the colonies that grew after 1 day's cultivation at 35° C. were Streptomycin-resistant strains.

Example 8

A loopful of each of the strains obtained in Example 7 and the parent strain from which they were derived was inoculated in 2 ml of the liquid medium having a composition of Formulation 3 below charged in a test tube with a Morton plug. Each strain was cultivated at 35° C. for 18 hours with shaking, and the culture broth was centrifuged to obtain a supernatant, whose lipase activity was determined by the aforementioned method. As a result, Streptomycin-resistant strains having high lipase-productivities as shown in Table 5 were obtained. About 60% of the Streptomycin-resistant strains thus obtained had lipase productivities higher than the parent strain. Their lipase productivities were by about 1.5 to 2 times as high as that of the parent strain. Strain No. 31 which had the highest productivity among the strains listed in Table 5 was named Pseudomonas SD703,-which was deposited at Fermentation Research Institute, Agency of Industrial Science and Technology, Ministry of International Trade and Industry, Japan under Accession No. FERM P-13307 on Nov. 26, 1992 and transferred to the deposit under "Budapest Treaty on the International Recognition of the Deposit of Microorganisms for the Purpose of Patent Procedure" under Accession No. FERM BP-4292 on May 12, 1993.

| Formulation 3 | |
| --- | --- |
| Soybean powder | 2.0% |
| Glucose | 2.0% |
| Amonium sulfate | 0.1% |
| Urea | 0.1% |
| Yeast extracts | 0.5% |
| Dipotassium hydrogen phosphate | 0.5% |
| Magnesium sulfate heptahydrate | 0.1% |
| Sodium carbonate | 0.3% |

The media were sterilized in an autoclave at 121° C. for 20 minutes.

TABLE 5

| Strain | Resistance to Streptomycin | Lipase Activity |
| --- | --- | --- |
| No. 31 | >250 ppm | 6.5 U/ml |
| No. 41 | >250 ppm | 4.8 U/ml |
| No. 51 | >250 ppm | 4.3 U/ml |
| NCIMB10541 | <50 ppm | 3.0 U/ml |

Example 9

A loopful of each of strain SD703 and the parent strain from which it was derived was inoculated in 2 ml of the liquid medium having a composition of Formulation 4 below charged in a test tube with a Morton plug. Each strain was cultivated at 35° C. for 18 hours with shaking, and the culture broth was centrifuged to obtain a supernatant, whose lipase activity was determined by the aforementioned method. Results obtained are shown in Table 6 below.

| Formulation 4 | |
| --- | --- |
| Casamino acid | 2.0% |
| Glucose | 2.0% |
| Diammonium hydrogen phosphate | 0.1% |
| Dipotassium hydrogen phosphate | 0.3% |
| Yeast extracts | 0.5% |
| Magnesium sulfate heptahydrate | 0.1% |
| Sodium carbonate | 0.3% |
| Tween 80 | 0.7% |

The media were sterilized in an autoclave at 121° C. for 20 minutes.

TABLE 6

| Strain | Lipase Activity |
| --- | --- |
| SD703 | 20.5 U/ml |
| NCIMB10541 | 9.4 U/ml |

Example 10

Strain NCIMB10541 was cultivated on a plate medium of Formulation 2 above at 35° C. for 16 hours, and a loopful amount thereof was inoculated in 5 ml of a liquid medium having a composition of Formulation 1 above excepting agar, charged in a test tube with a Morton plug. The strain was cultivated for 5 hours, and the culture broth was centrifuged. The bacterial cells thus collected were suspended in physiological saline. An N-methyl-N'-nitro-N-nitrosoguanidine (NTG) solution was added thereto to a final concentration of 100 ppm, and the mixture was left to stand at 30° C. for 10 minutes. Then, bacterial cells were collected by centrifugation, washed with physiological saline, and cultivated with shaking at 35° C. for 16 hours in the liquid medium having a composition of Formulation 2 excepting agar. The culture broth was spread over a plate medium having a composition of Formulation 2 containing 100 ppm of Carbenicillin after it was diluted properly so that a viable cell population became about $10^8$ cells per plate. Most of the colonies that grew after 1 day's cultivation at 35° C. were Carbenicillin-resistant strains.

Example 11

A loopful of each of the strains obtained in Example 10 and the parent strain from which they were derived was inoculated in 2 ml of the liquid medium having a composition of Formulation 3 above charged in a test tube with a Morton plug. Each strain was cultivated at 35° C. for 18 hours with shaking, and the culture broth was centrifuged to obtain a supernatant, whose lipase activity was determined by the aforementioned method. As a result, Carbenicillin-resistant strains having high lipase-productivities as shown in Table 7 were obtained. Most of the Carbenicillin-resistant strains thus obtained had lipase productivities higher than the parent strain. Their lipase productivities were by about 2 to 2.5 times as high as that of the parent strain. Strain No. 15 which had the highest productivity among the strains listed in Table 7 was named *Pseudomonas mendocina* SD704, which was deposited at Fermentation Research Institute, Agency of Industrial Science and Technology, Ministry of International Trade and Industry, Japan under Accession No. FERM P-13357 on December 25, 1992 and transferred to the deposit under "Budapest Treaty on the International Recognition of the Deposit of Microorganisms for the Purpose of Patent Procedure" under Accession No. FERM BP-4293 on May 12, 1993.

TABLE 7

| Strain | Resistance to Carbenicillin | Lipase Activity |
| --- | --- | --- |
| No. 15 | >400 ppm | 8.5 U/ml |
| No. 31 | >400 ppm | 7.5 U/ml |
| No. 36 | >400 ppm | 7.1 U/ml |
| NCIMB10541 | <100 ppm | 3.5 U/ml |

Example 12

A loopful of each of strain SD704 strain and the parent strain from which it was derived was inoculated in 2 ml of the liquid medium having a composition of Formulation 4 above charged in a test tube with a Morton plug. Each strain was cultivated at 35° C. for 18 hours with shaking, and the culture broth was centrifuged to obtain a supernatant, whose lipase activity was determined by the aforementioned method. Results obtained are shown in Table 8 below.

TABLE 8

| Strain | Lipase Activity |
| --- | --- |
| SD704 | 24.5 U/ml |
| NCIMB10541 | 10.1 U/ml |

Examples 13 to 30 Evaluation of Washing-1

Washing tests were carried out using the alkaline lipase powder obtained in Example 2. As cloth stained with dirt, there was used a defatted cotton cloth (15 cm×15 cm) which was soiled with 70 mg of triolein dissolved in benzene and dried. Washing machine used was Terg-O-Tometer. Various commercially available detergents were each dissolved in 1 liter of deionized water in a standard use concentration. To each resulting solution were added calcium chloride to adjust its calcium concentration to a determined level, and further the alkaline lipase to a predetermined concentration. In some cases, protease API-21 (Japanese Patent Publication No. 55118/1985) was added thereto to a predetermined concentration. Four to six triolein-soiled cloths per liter of the washing solution were charged in the washing machine, and washed at a washing temperature within the range of 20° to 35° C. and at 120 rpm for 30 minutes. After the washing, the cloths were rinsed twice each with 1 liter of the aforementioned calcium-added deionized water, and dried. The amounts of triolein on the soiled cloths before and after the washing were obtained by extracting triolein with n-hexane, and determining the amount of triolein by the aforementioned TLC-FID method. Washing Efficiency and enzyme addition effect of the lipase-added detergent were given in accordance with the following formulae.

Washing Efficiency (%) =

[(Amount of triolein on soiled cloth before washing − Amount of triolein on soiled cloth after washing)/Amount of triolein on soiled cloth before washing)] × 100

Effect of Enzyme Addition (%) =

[Washing Efficiency (%) when lipase was added] − [Washing

Efficiency (%) when no lipase was added (when there was only a detergent)]

Results obtained are shown in Table 9.

TABLE 9

| | | Washing Conditions | | | | | | |
| --- | --- | --- | --- | --- | --- | --- | --- | --- |
| Example | Detergent | Concentration of Detergent (g/liter) | pH upon Washing | Hardness* (mg/liter) | Temperature (°C.) | Lipase (U/liter) | Protease (nkatal/liter) | Effect of Enzyme Addition (%) |
| 13 | A | 5.0 | 10.8 | 150 | 30 | 1950 | 0 | 21.1 |
| 14 | A | 5.0 | 10.8 | 150 | 30 | 1950 | 100 | 20.8 |
| 15 | A | 5.0 | 10.8 | 150 | 30 | 1950 | 300 | 20.1 |
| 16 | B | 5.0 | 10.4 | 150 | 30 | 980 | 0 | 10.4 |
| 17 | B | 5.0 | 10.4 | 150 | 30 | 1950 | 0 | 11.9 |
| 18 | B | 5.0 | 10.4 | 150 | 30 | 3900 | 0 | 14.3 |
| 19 | E | 2.0 | 10.0 | 60 | 35 | 2000 | 0 | 7.6 |
| 20 | F | 0.83 | 11.1 | 20 | 30 | 1200 | 0 | 29.8 |
| 21 | F | 0.83 | 11.1 | 20 | 30 | 2400 | 0 | 40.2 |
| 22 | F | 0.83 | 11.1 | 20 | 30 | 2400 | 150 | 38.8 |
| 23 | F | 0.83 | 11.1 | 20 | 30 | 2400 | 300 | 38.0 |
| 24 | F | 0.83 | 11.1 | 20 | 30 | 3600 | 0 | 36.8 |
| 25 | F | 0.83 | 11.1 | 20 | 30 | 4800 | 0 | 40.5 |
| 26 | G | 0.83 | 10.6 | 20 | 30 | 980 | 0 | 12.7 |
| 27 | G | 0.83 | 10.6 | 20 | 30 | 1950 | 0 | 24.0 |
| 28 | G | 0.83 | 10.6 | 20 | 30 | 3900 | 0 | 35.1 |
| 29 | H | 2.00 | 7.6 | 60 | 35 | 2000 | 0 | 32.0 |
| 30 | I | 1.25 | 9.0 | 20 | 20 | 2000 | 0 | 31.5 |

*Expressed in terms of calcium ion

From the results shown in Table 9, it is clear that the detergent compositions blended with the alkaline lipase of the present invention gave rise to increased washing efficiency against lipid staining.

Examples 31 to 33: Evaluation of Washing-2

The same procedure as in Example 17 was repeated except that the alkaline lipase powder obtained in Example 4 was used instead of the alkaline lipase powder obtained in Example 2. Washing Efficiency and the effect of enzyme addition were calculated in accordance with the same formulae as described in Examples 13 to 30 above.

Results obtained are shown in Table 10.

TABLE 10

| | | Washing Conditions | | | | | | |
|---|---|---|---|---|---|---|---|---|
| | Alkaline | Detergent | | pH | | | | Effect of |
| Ex. | Lipase Produced by NCIMB | Kind | Concentration (g/liter) | upon Washing | Hardness* (mg/liter) | Temperature (°C.) | Lipase (U/liter) | Protease (nkatal/liter) | Enzyme Addition (%) |
| 31 | 10541 | B | 5.0 | 10.4 | 150 | 30 | 1950 | 0 | 10.2 |
| 32 | 10542 | B | 5.0 | 10.4 | 150 | 30 | 1950 | 0 | 11.3 |
| 33 | 10543 | B | 5.0 | 10.4 | 150 | 30 | 1950 | 0 | 10.9 |

*Expressed in terms of calcium ion

From the results shown in Table 10, it is clear that the detergent compositions blended with the alkaline lipase produced by a strain belonging to *Pseudomonas mendocina* also gave rise to increased washing efficiency against lipid soiling.

Comparative Examples 1 to 3: Evaluation of Washing on Other Lipases

Washing was performed in the same manner as in Example 17 or Example 23 using commercially available detergent B or F, respectively, except that a lipase derived from *Humicola lanuginosa* described in Japanese, Patent Application Laid-Open No. 62990/1973, a lipase derived from *Pseudomonas fragi* 22–39B described in Japanese Patent Application Laid-Open No. 280274/1986, or a lipase derived from *Achromobacter sp.* (Seikagaku Kogyo Co., Ltd.), instead of the alkaline lipase of the present invention to study enzyme addition effects. Results obtained are shown in Table 11.

TABLE 11

| Comparative Example. | Kind of Lipase | Washing Conditions | | | | Effect of Enzyme Addition (%) |
|---|---|---|---|---|---|---|
| | | Detergent | Hardness* (mg/liter) | Lipase (U/liter) | Protease (nkatal/liter) | |
| 1 | Lipase produced by *Humicola lanuginosa* | F | 20 | 2400 | 300 | 8.8 |
| 2 | Lipase produced by *Pseudomonas fragi* | B | 150 | 1950 | 0 | 7.3 |
| 3 | Lipase produced by *Acromobacter sp.* | B | 150 | 1950 | 0 | 3.0 |

*Expressed in terms of calcium ion

From the results shown in Table 11, it is evident that the comparative detergent compositions as shown in Table 11 differ from the detergent compositions blended with the alkaline lipase of the present invention in the effect of enzyme addition.

From these results, it was confirmed that the addition of the alkaline lipase of the present invention resulted in increase in the washing efficiency by at least 10% as high as that obtained in the case where no alkaline lipase was added.

What is claimed is:

1. An alkaline lipase obtained from a culture of a strain of *Pseudomonas mendocina* having the following properties:

(1) an optimum pH of 8±1, as measured using triolein emulsion as a substrate:

(2) an optimum temperature of 59° C.±3° C., as measured using triolein emulsion as a substrate;

(3) a molecular weight of 28,000±2,000 as measured by electrophoresis using SDS polyacrylamide;

(4) an isoelectric point of 4.5±1.5 as measured by iso-electric focusing polyacrylamide gel electrophoresis; and (5) an inhibition of lipase activity by a detergent component of not higher than 50% as measured using sodium linear-alkylbenzensulfonate as said detergent component.

2. The alkaline lipase as claimed in claim 1, wherein said alkaline lipase is obtained from a culture of *Pseudomonas mendocina* SD702 (FERM P-12944/FERM BP-4291) or its mutants which have an ability to produce the lipase.

3. An enzyme-containing detergent composition comprising, as an enzyme additive, said alkaline lipase as described in claim 1 produced by a microorganism *Pseudomonas mendocina*.

4. An enzyme-containing detergent composition comprising, as an enzyme additive, said alkaline lipase as described in claim 1 produced by a microorganism *Pseudomonas mendocina* SD702 (FERM P-12944/FERM BP-4291) or its mutants which have an ability of producing the lipase.

5. An enzyme-containing detergent composition comprising, as an enzyme additive, said alkaline lipase as described in claim 1 produced by a microorganism selected from the group consisting of *Pseudomonas mendocina* NCIMB10541, *Pseudomonas mendocina* NCIMB10542, *Pseudomonas mendocina* NCIMB10543, and mutants thereof which have an ability of producing the lipase.

6. An enzyme-containing detergent composition comprising, as an enzyme additive, said alkaline lipase as described in claim 1 produced by a microorganism *Pseudomonas mendocina* SD703 (FERM P-13307/FERM BP-4292).

7. An enzyme-containing detergent composition comprising, as an enzyme additive, said alkaline lipase as described in claim 1 produced by a microorganism *Pseudomonas mendocina* SD704 (FERM P-13357/FERM BP-4293).

8. The enzyme-containing detergent composition as claimed in any one of claims 3 through 7, wherein said enzyme additive is provided in the form of dustless granules.

9. The enzyme-containing detergent composition as claimed in any one of claims 3 through 7, wherein said enzyme additive is provided in the form of liquid or slurry.

10. The enzyme-containing detergent composition as claimed in any one of claims 3 through 7, further comprising an alkaline protease.

* * * * *